(12) United States Patent
Lee et al.

(10) Patent No.: US 7,098,341 B2
(45) Date of Patent: Aug. 29, 2006

(54) PROCESS FOR PREPARING HAPTENS FOR IMMUNOASSAY OF PHOSPHOROTHIOATE PESTICIDES

(75) Inventors: Yong-Tae Lee, 202-907 Shincheonjitown, 282 Hwanggeum-dong, Susung-gu, Taegu 706-795 (KR); Hye-Sung Lee, Taegu (KR); Yoo-Jung Kim, Taegu (KR)

(73) Assignee: Yong-Tae Lee, Taegu (KR)

( * ) Notice: Subject to any disclaimer, the term of this patent is extended or adjusted under 35 U.S.C. 154(b) by 39 days.

(21) Appl. No.: 10/876,748

(22) Filed: Jun. 25, 2004

(65) Prior Publication Data

US 2005/0033038 A1    Feb. 10, 2005

Related U.S. Application Data

(63) Continuation of application No. PCT/KR01/02301, filed on Dec. 29, 2001.

(30) Foreign Application Priority Data

Dec. 28, 2001 (KR) ............... 10-2001-0087382

(51) Int. Cl.
C07P 211/72   (2006.01)
(52) U.S. Cl. .............. 546/290; 546/300; 544/243
(58) Field of Classification Search ........... 546/290, 546/300; 544/243
See application file for complete search history.

(56) References Cited

OTHER PUBLICATIONS

Cho, et al., "Development of an ELISA for the Organophosphorus Insecticide Chlorpyrifos", 2002, Korean Chem. Soc., 23:481-487.
Park, et al., "Development of an ELISA for the Organophosphorus Insecticide Isofenphos", 2002, Korean Chem. Soc., 23:599-604.
Park e al., "Development of an Enzyme-Linked Immunosorbent Assay for the Organophosphorus Insecticide Cyanophos", 2002, Korean Chem. Soc., 23:605-609.
Park, et al., "Development of an Enzyme-Linked Immunosorbent Assay for the Organophosphorus Insecticide Bromphos", 2002 Korean Chem. Soc., 1399-1403.
Park, et al., "Development of an Enzyme-Linked Immunosorbent Assay for the Organophosphrous Fungicide Tolclofos-methyl", 2002, Korean Chem. Soc., 24:334-338.
Kim, et al., "Synthesis of haptens for immunoassay of organophosphorus pesticides and effect of heterology in hapten spacer arm length on immunoassay sensitivity", 2003, Analytica Chimica Acta, 475:85-96.
Kim, et al., "Synthesis of haptens of organophosphorus pesticides and development of enzyme-linked immunosorbent assays for parathion-methyl", 2003, Analytica Chimica Acta, 493:47-62 (2003).
Kim, et al., Investigation of the Effect of Hapten heterology on immunoassay sensitivity and development of an enzyme-linked immunosorbent assay for the organophosphorus insecticide fenthion, 2003, Analytica Chimica Acta, 494:29-40.
McAdam, et al., "Synthesis of Organothiophosphate Antigens for the Development of Specific Immunoassays", 1993, Aust. J. Chem., 46:959-967.
Skerritt, et al., "Approches to the Synthesis of Haptens for Immunoassay of Organophosphate and Synthetic Pyrethroid Insecticides", 1996, American Chemical Society Symposium Ser. 621: 124-149.

*Primary Examiner*—Joseph K. McKane
*Assistant Examiner*—Robert Shiao
(74) *Attorney, Agent, or Firm*—Knobbe, Martens, Olson & Bear, LLP

(57) ABSTRACT

The present invention relates to a process for preparing haptens for immunoassay of phosphorothioate pesticides, which comprises the steps of reacting O-methyl(ethyl) dichlorothiophosphate with a phenolic compound to obtain O-methyl(ethyl) O-aryl chlorothiophosphate, and reacting the O-(methyl)ethyl O-aryl chlorothiophosphate thus obtained with aminocarboxylic acid to give desired haptens. In accordance with the present invention, haptens having a structure of O-methyl(ethyl) O-aryl N-(carboxyalkyl)phosphoramidothioate or O-methyl(ethyl) O-aryl N-alkyl-N-(carboxyalkyl)phosphoramidothioate can be simply prepared with a high yield by employing two-step processes in a cost-efficient manner.

2 Claims, No Drawings

PROCESS FOR PREPARING HAPTENS FOR IMMUNOASSAY OF PHOSPHOROTHIOATE PESTICIDES

RELATED APPLICATIONS

This application is a continuation under 35 U.S.C. § 365 (c) claiming the benefit of the filing date of PCT Application No. PCT/KR01/02301 designating the United States, filed Dec. 29, 2001. The PCT Application was published in English as WO 03/055895 A1 on Jul. 10, 2003. The contents of the international application No. PCT/KR01/02301 and the publication WO 03/055895 A1 are incorporated herein by reference in their entirety.

BACKGROUND OF THE INVENTION

1. Field of the Invention

The present invention relates to a process for preparing haptens for immunoassay of phosphorothioate pesticides, more specifically, to a process for preparing haptens for immunoassay of organophosphorus phosphorothioate pesticides, by reacting O-methyl(ethyl) dichlorothiophosphate with a phenolic compound to obtain O-methyl(ethyl) O-aryl chlorothiophosphate, and reacting O-methyl(ethyl) O-aryl chlorothiophosphate thus obtained with aminocarboxylic acid.

2. Background of the Invention

Since Schrader's discovery of an organophosphorus compound possessing insecticidal activity in the 1930's, lots of organophosphorus pesticides with high biological activities have been actively developed in the art, in line with the movement of prohibiting the use of organochlorine pesticides. Nowadays, organophosphorus pesticides hold a large majority in current pesticides. Further, it is remarkable that about 100,000 of them have been identified to possess insecticidal activity, and more than 100 of them are commercially available.

Organophosphorus pesticides are classified into phosphate, phosphorothioate, phosphorothiolate, phosphorodithioate, phosphonate, phosphonothioate, phosphonodithioate, phosphorothiolothinate, and phosphoroamidate, depending on their chemical structures around a phosphorus atom (see: Table 1). Among them, phosphorothioate and phosphorodithioate are considered to be the most important pesticides in agriculture and have become the main subject of assaying residual pesticides.

The assay of residual pesticide has been carried out mainly by the aid of GC or HPLC, both of which have innate disadvantages that a time-consuming step of pre-treatment, high-priced machinery and tools, and labors with professional techniques are required and, in the case of GC, it is impossible to assay thermolabile material and in the case of HPLC, it is hard to assay pesticides having no chromophore. To solve these problems, many attempts to employ an immunoassay method for analysing residual pesticides, which was mainly used for assay of bio-components or a clinical diagnosis, began to be made in the 1970's. Immunoassay of residual pesticides is more favorable than the conventional methods in the points that: it is highly sensitive; pre-treatment of samples is not required; and, it costs a less deal since it allows the rapid assay of multiple samples in a simultaneous manner.

Immunoassay is based on the specific binding with a high affinity between antibodies and antigens. Thus, to develop immunoassay, an appropriate antigen should be prepared to generate antibodies against a substance to be assayed. However, low-molecular weight materials, such as pesticides, cannot serve as antigens in themselves and thus, antibodies cannot be generated. Under the circumstances, the need has been raised that haptens having a similar structure to pesticide and a functional groups capable of forming covalent bonds with proteins, should be synthesized for preparing pesticide-specific antigens. Also, synthesis of haptens has been required for preparing an enzyme tracer and a coating antigen, a competitor to be used for a competitive-immunoassay method.

TABLE 1

Classification of organophosphorus pesticides

| Class | Structure | Example |
|---|---|---|
| Phosphate | RO-P(=O)(OR)-O-X | Dichlorvos |
| Phosphorothioate | RO-P(=S)(OR)-O-X | Parathion |
| Phosphorothiolate | RO-P(=O)(OR)-S-X | Omethoate |
| Phosphorodithioate | RO-P(=S)(OR)-S-X | Malathion |
| Phosphonate | RO-P(=O)(R)-O-X | trichlorfon |
| Phosphonothioate | RO-P(=S)(R)-O-X | EPN |
| Phosphonodithioate | RO-P(=S)(R)-S-X | Fonfos |
| Phosphorothiolothionate | RS-P(=O)(RS)-O-X | Ethoprop |
| Phosphoroamidate | $R_2N$-P(=O)($R_2N$)-X | Dimefox |

In general, haptens used for immunoassay of phosphorothioate pesticides have a chemical structure as following:

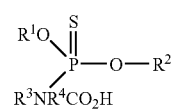

wherein,

R¹ is methyl or ethyl group;

R² is aryl group;

R³ is hydrogen or alkyl group; and,

R⁴ is alkylidene group.

Among the above haptens, haptens having the structure in which R³ is hydrogen and R⁴ is di- or pentamethylene group have been synthesized so far. The haptens having the structure in which R³ is hydrogen and R⁴ is dimethylene group have been synthesized by a process comprising the steps of: (i) reacting 3-aminopropanoic acid (1) with benzylchloroformate to obtain 3-(benzyloxycarbonylamino)propanoic acid (2); (ii) reacting 3-(benzyloxycarbonylamino)propanoic acid (2) thus obtained with tert-butanol in the presence of dicyclohexalcarbodiimide(DCC) to obtain tert-butyl 3-(benzyloxycarbonylamino)propanoate (3); (iii) eliminating amino protective group from tert-butyl 3-(benzyloxycarbonylamino)propanoate (3) thus obtained by way of hydrogenation using a catalyst to obtain tert-butyl-3-aminopropanoate (4); (iv) reacting tert-butyl 3-aminopropanoate (4) thus obtained with O-methyl dichlorothiophosphate (5) to obtain tert-butyl 3-[chloro(methoxyl)phosphorothioylamino]propanoate (6); (v) reacting tert-butyl 3-[chloro(methoxyl) phosphorothioylamino]propanoate thus obtained with a sodium salt of phenol (7) to obtain tert-butyl 3-[methoxy(aryloxy)phosphorothioylamino]propanoate (8); and, (vi) removing tert-butyl protective group from tert-butyl 3-[methoxy(aryloxy)phosphorothioylamino]propanoate (8) with an aid of trifluoroacetic acid(TFA) to obtain 3-[methoxy(aryloxy)phosphorothioylamino]propanoic acid (9).

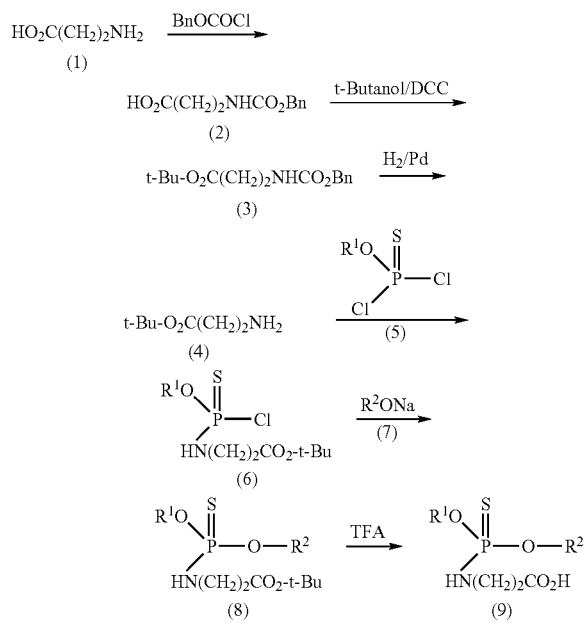

It has been known that O-alkyl O-aryl N-(2-carboxyalkyl) phosphoramidothioates synthesized by the above process is can be a haptens highly preferable for generating antibodies for phosphothioate pesticides. However, the said process has revealed shortcomings that it is very complicated, time- and cost-consuming and poorly yielded, since the said method goes through a process comprising total six steps or seven steps provided a step of preparing a sodium salt of phenol is added.

Under the circumstances, there are strong reasons for developing a process for preparing haptens for immunoassay of phosphothioate pesticide in a more efficient manner.

SUMMARY OF THE INVENTION

The present inventors have made an effort to develop an efficient process for preparing haptens for immunoassay of phosphothioate pesticide, and found that haptens having a structure of O-methyl(ethyl) O-aryl N-(carboxyalkyl)phosphoramidothioate or O-methyl(ethyl) O-aryl N-alkyl-N-(carboxyalkyl)phosphoramidothioate can be prepared by the process comprising the steps of: reacting O-methyl(ethyl) dichlorothiophosphate with a phenolic compound to obtain O-methyl(ethyl) O-aryl chlorothiophosphate; and, reacting O-methyl(ethyl) O-aryl chlorothiophosphate thus obtained with aminocarboxylic acid whose carboxylic group is not protected.

A primary object of the present invention is, therefore, to provide a process for preparing haptens for immunoassay of organophosphorus phosphorothioate pesticides.

DETAILED DESCRIPTION OF THE INVENTION

A process for preparing haptens for immunoassay of organophosporous phosphorothioate pesticides comprises the steps of: (i) reacting a compound (10) with a phenolic compound (11) and K₂CO₃ in acetonitrile at 4° C. for 30 to 90 min to obtain a compound (12); and, (ii) reacting the compound (12) with a compound (13) and KOH in methanol at 4° C. for 3 to 5 min to obtain a compound (14). The phosphorothioate pesticides includes fenthion, fenitrothion, parathion, parathion-methyl, bromophos-methyl, bromophos-ethyl, chlorpyrifos, chlorpyrifos-methyl, diazinon, isofenphos and pyrimiphos-methyl.

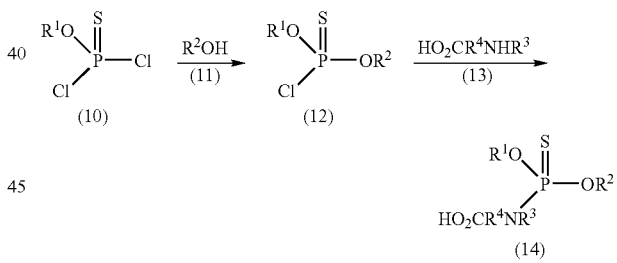

wherein,

R¹ is methyl or ethyl group;

R² is aryl group;

R³ is hydrogen or alkyl group; and,

R⁴ is alkylidene polymethylene or substituted polymethylene group.

The present invention is further illustrated in the following examples, which should not be taken to limit the scope of the invention.

EXAMPLE 1

Preparation of Haptens for Immunoassay of Phosphorothioate Pesticides

O-methyl(ethyl) O-aryl chlorothiophosphate, which was obtained by reacting O-methyl(ethyl) dichlorothiophosphate with phenol, was reacted with aminocarboxylic acid to give a hapten for immunoassay of phosphorothioate pesticides: to 46 mmol of O-methyl(ethyl) dichlorothiophosphate (10) dissolved in 30 mL of acetonitrile was added 45 g of ground K$_2$CO$_3$ and 42 mmol of phenol (11) dissolved in 30 mL of acetonitrile, and the mixture was stirred for 1 hour at room temperature. Then, the reaction mixture was filtered with cellite, the solvent was evaporated from the filtrate, and the remnant was subject to silica-gel column chromatography equilibrated with benzene/hexane (1:1, v/v) or hexane/ethylacetic acid (10:1, v/v), to obtain oily compound of O-methyl(ethyl) O-aryl chlorothiophosphate (12).

A solution of 2.1 mmol of O-methyl(ethyl) O-aryl chlorothiophosphate (12) thus obtained in 3 mL of methanol, cooled in ice-water bath, was stirred for 3 to 5 min with a gradual addition of 5.2 mmol (292 mg) of KOH and 2.6 mmol of aminocarboxylic acid (13) dissolved in 1.7 mL of methanol. In a case that aminocarboxylic acid is hydrochloride, the molar ratio of KOH to aminocarboxylic acid was three. The reaction solution was poured into a separatory funnel, and the product was extracted with the addition of 1N HCl and chloroform. The extract was dehydrated over MgSO$_4$, the solvent was evaporated, and the remnant was subject to silica-gel column chromatography equilibrated with chloroform:ethylacetic acid:acetic acid (65:35:1, v/v/v), to obtain a compound (14) for the immunoassay of phosphorothioate pesticide. In the following chemical reaction scheme, R$^1$ is methyl or ethyl group, R$^2$ is aryl group, R$^3$ is hydrogen or alkyl group, and R$^4$ is alkylidene polymethylene or substituted polymethylene group.

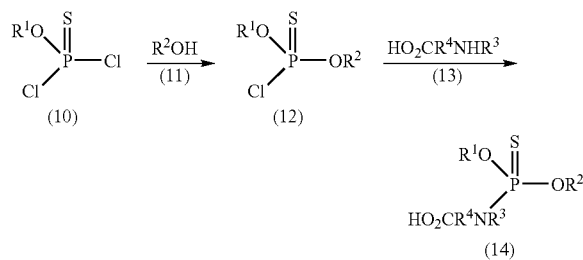

EXAMPLE 2

Synthesis of Haptens for Immunoassay of Phosphorothioate Pesticides

By employing the method of Example 1, haptens with various substituents (R$^1$, R$^2$, R$^3$ and R$^4$) were synthesized for immunoassay of phosphorothioate pesticides such as parathion-methyl, chlorpyrifos and isofenphos. Various structures of haptens for immunoassay of phosphorothioate pesticide are shown in Table 2 below, where Ph and Pyr represent benzene ring and pyridinyl group, respectively.

TABLE 2

Various structures of haptens for immunoassay of phosphorothioate pesticides

| | Phosphorothioate pesticides | R$^1$ | R$^2$ | R$^3$ | R$^4$ |
|---|---|---|---|---|---|
| A | parathion-methyl | CH$_3$ | Ph-p-NO$_2$ | H | —(CH$_2$)$_3$— |
| B | parathion-methyl | CH$_3$ | Ph-p-NO$_2$ | H | —(CH$_2$)$_5$— |
| C | parathion-methyl | CH$_3$ | Ph-p-NO$_2$ | CH$_3$ | —(CH$_2$)$_3$— |
| D | chlorpyrifos | CH$_3$CH$_2$ | Pyr-(3,5,6-trichloro) | H | —(CH$_2$)$_3$— |
| E | chlorpyrifos | CH$_3$CH$_2$ | Pyr-(3,5,6-trichloro) | H | —(CH$_2$)$_5$— |
| F | chlorpyrifos | CH$_3$CH$_2$ | Pyr-(3,5,6-trichloro) | CH$_3$ | —(CH$_2$)$_3$— |
| G | isofenphos | CH$_3$CH$_2$ | Ph-o-CO$_2$CH(CH$_3$)$_2$ | H | —CH(CH$_3$)CH$_2$— |

$^1$H NMR analysis revealed that the synthesized haptens have the same spectrum as those of the structures of haptens shown in Table 2. In $^1$H NMR spectrum, the value of chemical shift (ppm) is given relative to internal tetramethylsilane and the values of coupling constant (J) is expressed in Hz and s, d, t, q, qn, sp, ar and m represent singlet, doublet, triplet, quartet, quintet, septet, aromatic and multiplet, respectively.

EXAMPLE 2-1

Synthesis of Hapten A

By employing the method of Example 1, hapten A(R$^1$=methyl, R$^2$=p-nitrophenyl, R$^3$=hydrogen and R$^4$=(CH$_2$)$_3$ was synthesized: to 4.59 g (28 mmol) of O-methyl dichlorothiophosphate dissolved in 20 mL of acetonitrile was added 20 g of ground K$_2$CO$_3$ and 3.00 g (22 mmol) of 4-nitrophenol dissolved in 15 mL of acetonitrile, and the mixture was stirred for 1 hour at room temperature. Then, the reaction mixture was filtered with cellite, the solvent was evaporated solvent from the filtrate, and the remnant was subject to silica-gel column chromatography equilibrated with benzene/hexane (1:1, v/v) to obtain oily compound of O-methyl O-(4-nitrophenyl)chlorothiophosphate. The yield of the compound was 70% and its NMR data was as follows:

$^1$H NMR(300 MHz, CDCl$_3$): δ8.28(2H, d, J=6.1, ar), 7.42(2H, d, J=7.2, ar), 4.03(3H, d, J=16.5, CH$_3$OP)

A solution of 500 mg (1.9 mmol) of O-methyl O-(4-nitrophenyl)chlorothiophosphate thus obtained in 3 mL of methanol, cooled in ice-water bath, was stirred for 3 to 5 min with a gradual addition of 274 mg (4.9 mmol) of KOH and 229 mg (2.2 mmol) of aminobutyric acid in 1.7 mL of methanol. The reaction solution was poured into a separatory funnel, and the product was extracted with an addition of 1N HCl and chloroform. The extract was dehydrated over MgSO$_4$, the solvent was evaporated, and the remnant was subject to silica-gel column chromatography equilibrated with chloroform:ethylacetic acid:acetic acid (65:35:1, v/v/v), to obtain a hapten A of Table 2. The yield of hapten A was 81% and its NMR data was as follows:

$^1$H NMR(300 MHz, CDCl$_3$): δ8.24 (2H, d, J=8.9, ar), 7.38 (2H, d, J=8.3, ar), 3.81 (3H, d, J=14.1, CH$_3$OP), 3.47 (1H, dxt, J=14.8 & 7.0, NH), 3.17 (2H, dxq, J=13.6 & 6.9, NCH$_2$), 2.46 (2H, t, J=7.0, CH$_2$CO$_2$), 1.88 (2H, qn, J=7.0, CH$_2$CH$_2$CH$_2$)

EXAMPLE 2-2

Synthesis of Hapten B

By employing the method of Example 1, hapten B($R^1$=methyl, $R^2$=p-nitrophenyl, $R^3$=hydrogen and $R^4$=$(CH_2)_5$) was synthesized: a solution of 500 mg (1.9 mmol) of O-methyl O-(4-nitrophenyl)chlorothiophosphate in 3 mL of methanol, cooled in ice water bath, was stirred for 3 to 5 min with a gradual addition of 274 mg (4.9 mmol) of KOH and 291 mg (2.2 mmol) of 6-aminocaproic acid in 1.7 mL of methanol. Then, hapten B was synthesized in a similar manner as in Example 2-1, whose yield was 88% and NMR data was as follows:

$^1$H NMR(300 MHz, CDCl$_3$): δ8.24 (2H, d, J=8.9, ar), 7.37 (2H, dxd, J=9.2 & 1.4, ar), 3.81 (3H, d, J=14.2 CH$_3$OP), 3.34 (1H, dxt, J=15.5 & 6.8, NH), 3.09 (2H, dxq, J=13.8 & 6.9, NCH$_2$), 2.37 (2H, t, J=7.3, CH$_2$CO), 1.68 (2H, qn, J=7.6, NHCH$_2$CH$_2$), 1.56 (2H, m, CH$_2$CH$_2$CO), 1.40 (2H, m, (CH$_2$)$_2$CH$_2$CH$_2$(CH$_2$)$_2$)

EXAMPLE 2-3

Synthesis of Hapten C

By employing the method of Example 1, hapten C($R^1$=methyl, $R^2$=p-nitrophenyl, $R^3$=methyl and $R^4$=$(CH_2)_3$ was synthesized: a solution of 202 mg (0.76 mmol) of O-methyl O-(4-nitrophenyl)chlorothiophosphate in 1.5 mL of methanol, cooled in ice-water bath, was stirred for 5 min with a gradual addition of 207 mg (3.7 mmol) of KOH and 154 mg (1.0 mmol) of 4-(methylamino)butyric acid(salt of hydrochloride) in 1.5 mL of methanol. Then, hapten C was synthesized in a similar manner as in Example 2-1, whose yield was 70% and its NMR data was as follows:

$^1$H NMR (400 MHz, CDCl$_3$): δ8.23 (2H, d, J=9.0, ar), 7.31 (2H, d, J=9.0, ar), 3.76 (3H, d, J=14.1, CH$_3$OP), 3.36 (2H, dxq, NCH$_2$), 2.86 (3H, d, J=11.0, CH$_3$N), 2.40 (2H, t, J=7.5, CH$_2$CO$_2$), 1.89 (2H, qn, J=7.0, CH$_2$CH$_2$CH$_2$)

EXAMPLE 2-4

Synthesis of Hapten D

By employing the method of Example 1, hapten D($R^1$=ethyl, $R^2$=3,5,6-trichloro-2-pyridyl, $R^3$=hydrogen and $R^4$=$(CH_2)_3$) was synthesized: to 3.52 g (20 mmol) of O-ethyl dichlorothiophosphate dissolved in 20 mL of acetonitrile was added 10 g of ground K$_2$CO$_3$ and 3.00 g (15 mmol) of 3, 5, 6-trichloro-2-pyridinol dissolved in 5 mL of acetonitrile, and the mixture was stirred for 1 hour at room temperature. Then, the reaction mixture was filtered with cellite, the solvent was evaporated, and the remnant was subject to silica-gel column chromatography equilibrated with benzene/hexane (1:1, v/v) solvent to obtain oily compound of O-ethyl O-(3, 5, 6-trichloro-2-pyridyl)chlorothiophosphate. The yield of the said compound was 65% and its NMR data was as follows:

$^1$H NMR(300 MHz, CDCl$_3$): δ7.91 (1H, d, J=1.3, ar), 4.52 (2H, qxd, J=11.0 & 7.1, CH$_2$CH$_3$), 1.51 (3H, txd, J=7.1 & 1.1, CH$_2$CH$_3$)

A solution of 0.50 g (1.5 mol) of O-ethyl O-(3, 5, 6-trichloro-2-pyridyl)chlorothiophosphate thus obtained was dissolved in 3 mL of methanol, cooled in ice-water bath, was stirred for 3 to 5 min with a gradual addition of 0.205 g (3.23 mmol) of KOH and 0.166 g (1.6 mmol) of aminobutyric acid in 1.7 mL of methanol. Then, hapten D was synthesized in a similar manner as in Example 2-1, whose yield was 54% and its NMR data was as follows:

$^1$H NMR(300 MHz, CDCl$_3$): δ7.85 (1H, d, J=0.9, ar), 4.34 (2H, qxd, J=9.5 & 7.1, CH$_2$CH$_3$), 3.54 (1H, dxt, J=11.4 & 6.6, NH), 3.25 (2H, dxq, J=13.1 & 6.8, NHCH$_2$), 2.51 (2H, t, J=7.2, CH$_2$CO$_2$), 1.93 (2H, qn, J=6.9, CH$_2$CH$_2$CH$_2$), 1.41 (3H, t, J=7.1, CH$_2$CH$_3$)

EXAMPLE 2-5

Synthesis of Hapten E

By employing the method of Example 1, hapten E($R^1$=ethyl, $R^2$=3,5,6-trichloro-2-pyridyl, $R^3$=hydrogen and $R^4$=$(CH_2)_5$ was synthesized: a solution of 0.50 g (1.5 mol) of O-ethyl O-(3, 5, 6-trichloro-2-pyridyl)chlorothiophosphate in 3 mL of methanol, cooled in ice-water bath, was stirred for 5 min with a gradual addition of 0.205 g (3.2 mmol) of KOH and 0.210 g (1.6 mmol) of 6-aminocaproic acid in 1.7 mL of methanol. Then, hapten E was synthesized in a similar manner as in Example 2-1, whose yield was 53% and its NMR data was as follows:

$^1$H NMR(250 MHz, CDCl$_3$): δ7.87 (1H, d, J=1.0, ar), 4.36 (2H, qxd, J=9.6 & 7.1, CH$_2$CH$_3$), 3.47 (1H, dxt, J=12.2 & 6.5, NH), 3.19 (2H, dxq, J=13.8 & 6.9, NHCH$_2$), 2.40 (2H, t, J=7.3, CH$_2$CO$_2$), 1.50 (6H, m, CH$_2$(CH$_2$)$_3$CH$_2$), 1.43 (3H, t, J=7.1, CH$_2$CH$_3$)

EXAMPLE 2-6

Synthesis of Hapten F

By employing the method of Example 1, hapten F($R^1$=ethyl, $R^2$=3,5,6-trichloro-2-pyridyl, $R^3$=methyl and $R^4$=$(CH_2)_3$) was synthesized: 0.50 g (1.5 mol) of O-ethyl O-(3, 5, 6-trichloro-2-pyridyl)chlorothiophosphate in 3 mL of methanol, cooled in ice-water bath, was stirred for 5 min with a gradual addition of 0.31 g (4.8 mmol) of KOH and 0.166 g (1.6 mmol) of 4-(methylamino)butyric acid(salt of hydrochloride) in 1.7 mL of methanol. Then, hapten F was synthesized in a similar manner as in Example 2-1, whose yield was 54% and its NMR data was as follows:

$^1$H NMR(300 MHz, CDCl$_3$): δ7.82 (1H, s, ar), 4.36 (2H, qxd, J=8.7 & 7.1, CH$_2$CH$_3$), 3.33 (2H, m, NCH$_2$), 2.87 (3H, d, J=12.3, CH$_3$N), 2.46 (2H, t, CH$_2$CO$_2$), 1.93 (2H, qn, CH$_2$CH$_2$CH$_2$), 1.43 (3H, t, J=7.1, CH$_2$CH$_3$)

EXAMPLE 2-7

Synthesis of Hapten G

By employing the method of Example 1, hapten G($R^1$=ethyl, $R^2$=2-(isopropyloxycarbonyl)phenyl, $R^3$=hydrogen and $R^4$=CH(CH$_3$)CH$_2$) was synthesized: to 2.96 g (17 mmol) of O-ethyl dichlorothiophosphate dissolved in 10 mL of acetonitrile was added 5 g of ground K$_2$CO$_3$ and 1.96 g (11 mmol) of isopropyl salicylate dissolved in 20 mL of acetonitrile, and the mixture was stirred for 40 min at room temperature. Then, the reaction mixture was filtered with cellite, the solvent was evaporated, and the remnant was subject to silica-gel column chromatography equilibrated with hexane/ethylacetatic acid (10:1, v/v) to obtain oily compound of O-ethyl O-[(2-isopropyloxycarbonyl)phenyl]chlorothiophosphate. The yield of the said compound was 61% and its NMR data was as follows:

$^1$H NMR(300 MHz, CDCl$_3$): δ7.93 (1H, dxd, J=7.7 & 1.2, ar), 7.55 (1H, dxd, J=8.5 & 1.5, ar), 7.48 (1H, txt, J=8.4 &

1.6, ar), 7.32 (1H, txt, J=7.5 & 1.5, ar), 5.25 (1H, sp, J=6.3, (CH$_3$)$_2$CH), 4.48 (2H, q, J=7.1, CH$_2$CH$_3$), 1.47 (3H, t, J=7.1, CH$_2$CH$_3$), 1.38 (6H, d, J=6.3, CH(CH$_3$)$_2$)

A solution of 67 mg (0.21 mol) of O-(2-isopropyloxycarbonyl)phenyl]chlorothiophosphate in 0.2 mL of methanol, cooled in ice-water bath, was stirred for 5 min with a gradual addition of 31 mg (0.55 mmol) of KOH and 26 mg (0.25 mmol) of DL-aminobutyric acid in 0.26 mL of methanol. The reaction solution was poured into a separatory funnel, and the product was extracted with an addition of 1N HCl and chloroform. The extract was dehydrated over MgSO$_4$, the solvent was evaporated, and the remnant was subject to silica-gel column chromatography equilibrated with chloroform:ethylacetic acid:acetic acid (29:9:1, v/v/v), to obtain a hapten G of Table 2. The yield of hapten G thus obtained was 66% and its NMR data was as follows:

$^1$H NMR(300 MHz, CDCl$_3$): δ7.81 (1H, dxd, J=8.9 & 1.2, ar), 7.60 (1H, dxqn, J=8.2 & 1.5, ar), 7.48 (1H, txt, J=7.9 & 1.8, ar), 7.21 (1H, txt, J=7.5 & 1.1, ar), 5.25 (1H, sp, J=6.2, (CH$_3$)$_2$CH), 4.29 (1H, q, J=9.5, NHCH), 4.20 (2H, q, J=7.1, CH$_2$CH$_3$), 3.97 (1H, sp, J=6.0, NHCH), 2.45 (2H, t, J=6.3, CH$_2$CO$_2$), 1.38 (3H, t, J=7.0, CH$_2$CH$_3$), 1.37 (6H, d, J=6.2, CH(CH$_3$)$_2$), 1.31 (3H, CHCH$_3$)

What is claimed is:

1. A process for preparing haptens for immunoassay of organophosporous phosphorothioate pesticides, which comprises the steps of:
   (i) reacting a compound (10) with a phenolic compound (11) and K$_2$CO$_3$ in acetonitrile at 4° C. for 30 to 90 min to obtain a compound (12); and,
   (ii) reacting the compound (12) with a compound (13) and KOH in methanol at 4° C. for 3 to 5 min to obtain a compound (14)

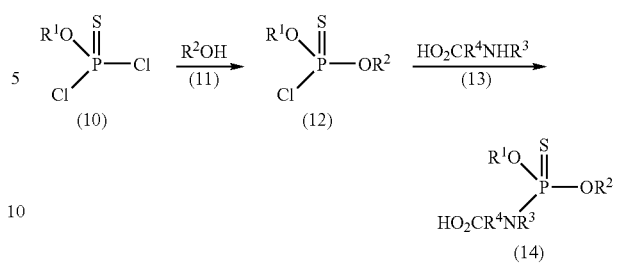

wherein,
   $R^1$ is methyl or ethyl group;
   $R^2$ is an optionally substituted pyridyl or pyrimidinyl group;
   $R^3$ is hydrogen or alkyl group; and,
   $R^4$ is polymethylene or substituted polymethylene group.

2. The process for preparing haptens for immunoassay of organophosporous phosphorothioate pesticide of claim 1, wherein the phosphorothioate pesticide is a substance selected from the group consisting of fenthion, fenitrothion, parathion, parathion-methyl, bromophos-methyl, bromophos-ethyl, chlorpyrifos, chlorpyrifos-methyl, diazinon, isofenphos and pyrimiphos-methyl.

* * * * *